United States Patent
Errico et al.

[11] Patent Number: 5,997,539
[45] Date of Patent: Dec. 7, 1999

[54] POLYAXIAL PEDICLE SCREW HAVING A COMPRESSION LOCKING ROD GRIPPING MECHANISM

[75] Inventors: Joseph P. Errico, Bedminster; Thomas J. Errico, Summit; James D. Ralph, Oakland; Stephen Tatar, Montville, all of N.J.

[73] Assignee: Spinal Concepts, Inc., Austin, Tex.

[21] Appl. No.: 09/070,268

[22] Filed: Apr. 30, 1998

Related U.S. Application Data

[63] Continuation of application No. 08/880,810, Jun. 23, 1997, which is a continuation-in-part of application No. 08/856,773, May 15, 1997.

[51] Int. Cl.$^6$ .................................................. A61B 17/56
[52] U.S. Cl. ............................. 606/61; 606/60; 623/16
[58] Field of Search .................... 606/61, 60, 62, 606/63, 64–75; 623/15, 16, 17, 18, 19

[56] References Cited

U.S. PATENT DOCUMENTS

| | | | |
|---|---|---|---|
| 5,261,909 | 11/1993 | Sutterlin et al. | 606/60 |
| 5,282,862 | 2/1994 | Baker et al. | |
| 5,306,307 | 4/1994 | Senter et al. | |
| 5,306,309 | 4/1994 | Wagner et al. | |
| 5,344,422 | 9/1994 | Frigg | |
| 5,403,314 | 4/1995 | Currier | |
| 5,425,772 | 6/1995 | Brantigan | |
| 5,437,669 | 8/1995 | Yuan et al. | |
| 5,501,684 | 3/1996 | Schlapfer et al. | |
| 5,507,746 | 4/1996 | Lin | |
| 5,569,246 | 10/1996 | Ojima et al. | |
| 5,584,831 | 12/1996 | McKay | |
| 5,591,166 | 1/1997 | Bernhardt et al. | 606/60 |
| 5,609,635 | 3/1997 | Michelson | |
| 5,643,259 | 7/1997 | Sasso et al. | |
| 5,683,392 | 11/1997 | Richelsoph et al. | |
| 5,785,711 | 7/1998 | Errico et al. | 606/61 |

FOREIGN PATENT DOCUMENTS

| | | |
|---|---|---|
| 97/38640 | 10/1997 | WIPO |
| 98/12976 | 4/1998 | WIPO |
| 98/14142 | 4/1998 | WIPO |

*Primary Examiner*—Michael Buiz
*Assistant Examiner*—Lien Ngo
*Attorney, Agent, or Firm*—Conley, Rose & Tayon, PC

[57] ABSTRACT

A polyaxial orthopedic device for use with rod implant apparatus includes a screw having a curvate ball top, a polyaxial head member having a socket into which the head of the screw is initially polyaxially nested, a vertical slot which renders the socket compressible, and a horizontal through hole having a tapered portion on one side of the vertical slot. A rod gripping cross-bar member, which is mounted through the through hole includes an axial split which permits the first end thereof to grip a rod, and then to be clamped onto the rod when the axial slot is narrowed. A nut is provided on the end of the cross-bar member which extend out from the through hole on the opposite end from the rod gripping mechanism. The advancement of the nut causes the cross-bar member to be compressed by the taper of the front portion of the through hole, thereby locking the rod in the gripping end thereof, and further provides the compression force necessary to compression lock the interior socket of the head against the ball top of the screw.

20 Claims, 6 Drawing Sheets

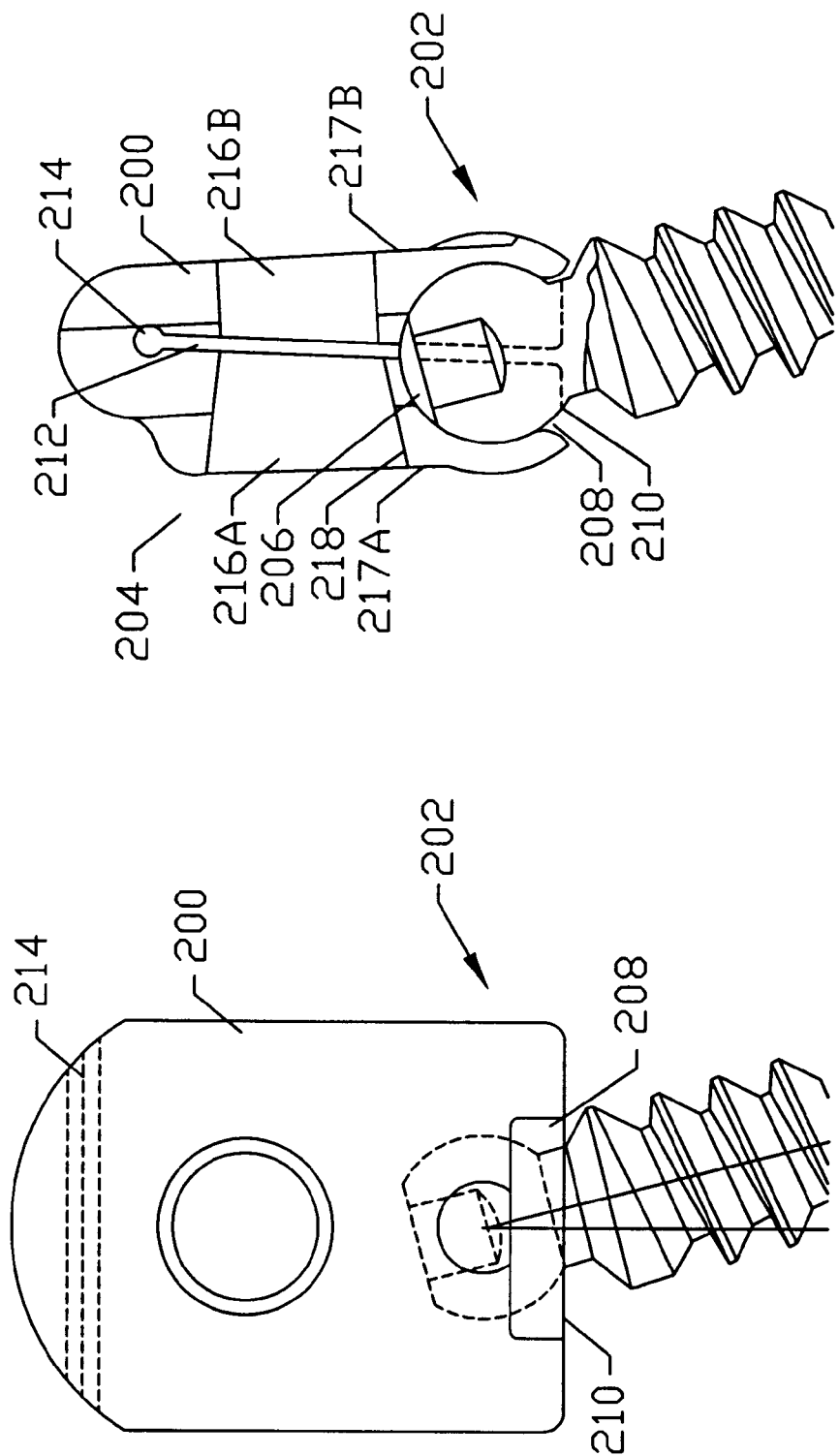

POLYAXIAL PEDICLE SCREW HAVING A COMPRESSION LOCKING ROD GRIPPING MECHANISM

CROSS-REFERENCE TO RELATED APPLICATION

This is a continuation of copending application Ser. No. 08/880,810, filed Jun. 23, 1997, which is a continuation-in-part of copending U.S. application Ser. No. 08/856,773, filed May 15, 1997.

BACKGROUND OF THE INVENTION

1. Field of the Invention

This invention relates generally to a polyaxial pedicle screw and, more particularly, to a screw for insertion into spinal bone having a polyaxial coupling and locking mechanism for mounting a stabilizing rod to a sequence of vertebrae.

2. Description of the Prior Art

The bones and connective tissue of an adult human spinal column consist of more than 20 discrete bones coupled sequentially to one another by a tri-joint complex which consist of an anterior disc and the two posterior facet joints, the anterior discs of adjacent bones being cushioned by cartilage spacers referred to as intervertebral discs. These more than 20 bones are anatomically categorized as being members of one of four classifications: cervical, thoracic, lumbar, or sacral. The cervical portion of the spine, which comprises the top of the spine, up to the base of the skull, includes the first 7 vertebrae. The intermediate 12 bones are the thoracic vertebrae, and connect to the lower spine comprising the 5 lumbar vertebrae. The base of the spine is the sacral bones (including the coccyx). The component bones of the cervical spine are generally smaller than those of the thoracic and lumbar spine. For the purposes of this disclosure, however, the word spine shall refer only to the cervical region.

Referring now to FIGS. 1, 2, and 3, top, side, and posterior views of a vertebral body, a pair of adjacent vertebral bodies, and a sequence of vertebral bodies are shown, respectively. The spinal cord is housed in the central canal 10, protected from the posterior side by a shell of bone called the lamina 12. The lamina 12 includes a rearwardly and downwardly extending portion called the spinous process 16, and laterally extending structures which are referred to as the transverse processes 14. The anterior portion of the spine comprises a set of generally cylindrically shaped bones which are stacked one on top of the other. These portions of the vertebrae are referred to as the vertebral bodies 20, and are each separated from the other by the intervertebral discs 22. The pedicles 24 comprise bone bridges which couple the anterior vertebral body 20 to the corresponding lamina 12.

The spinal column of bones is highly complex in that it includes over twenty bones coupled to one another, housing and protecting critical elements of the nervous system having innumerable peripheral nerves and circulatory bodies in close proximity. In spite of these complexities, the spine is a highly flexible structure, capable of a high degree of curvature and twist in nearly every direction. Genetic or developmental irregularities, trauma, chronic stress, tumors, and disease, however, can result in spinal pathologies which either limit this range of motion, or which threaten the critical elements of the nervous system housed within the spinal column. A variety of systems have been disclosed in the art which achieve this immobilization by implanting artificial assemblies in or on the spinal column. These assemblies may be classified as anterior, posterior, or lateral implants. As the classifications suggest, lateral and anterior assemblies are coupled to the anterior portion of the spine, which is the sequence of vertebral bodies. Posterior implants generally comprise pairs of rods, which are aligned along the axis along which the bones are to be disposed, and which are then attached to the spinal column by either hooks which couple to the lamina or attach to the transverse processes, or by screws which are inserted through the pedicles.

"Rod assemblies" generally comprise a plurality of such screws which are implanted through the posterior lateral surfaces of the laminae, through the pedicles, and into their respective vertebral bodies. The screws are provided with upper portions which comprise, or have mounted thereto, coupling elements for receiving and securing an elongate rod therethrough. The rod extends along the axis of the spine, coupling to the plurality of screws via their coupling elements. The rigidity of the rod may be utilized to align the spine in conformance with a more desired shape.

It has been identified, however, that a considerable difficulty is associated with inserting screws along a misaligned curvature and simultaneously exactly positioning the coupling elements such that the rod receiving portions thereof are aligned so that the rod can be passed therethrough without distorting the screws. Attempts at achieving proper alignment with fixed screws are understood to require increased operating time, which is known to enhance many complications associated with surgery. Often surgical efforts with such fixed-axes devices cannot be achieved, thereby rendering such instrumentation attempts entirely unsucessful.

The art contains a variety of attempts at providing instrumentation which permit a limited freedom with respect to angulation of the screw and the coupling element. These teachings, however, are generally complex, inadequately reliable, and lack long-term durability. These considerable drawbacks associated with prior art systems also include difficulty properly positioning the rod and coupling elements, and the tedious manipulation of the many small parts in the operative environment.

It is, therefore, the principal object of the present invention to provide a pedicle screw and coupling element assembly which provides a polyaxial freedom of implantation angulation with respect to rod reception.

In addition, it is an object of the present invention to provide such an assembly which comprises a reduced number of elements, and which correspondingly provides for expeditious implantation.

Accordingly it is also an object of the present invention to provide an assembly which is reliable, durable, and provides long term fixation support.

Other objects of the present invention not explicitly stated will be set forth and will be more clearly understood in conjunction with the descriptions of the preferred embodiments disclosed hereafter.

SUMMARY OF THE INVENTION

The preceding objects of the invention are achieved by the present invention which is a pedicle screw and rod coupling mechanism having a polyaxially rotating screw head which is selectively lockable at a desired fixed position with a cross-bar rod coupling mechanism as it is secured to the head. More specifically, the present invention comprises a bone screw having a semi-spherical ball top. The shaft of the screw is threaded for insertion and secure retention in vertebral bone. The ball-shaped top has a constant radius of curvature over the curvate portion thereof, which forms a ball top end of the screw, and includes a recess therein so that it may be driven by a screw driving mechanism into the pedicular bone. Onto the ball top of the screw is mounted a polyaxial head member, which is initially polyaxially disposed on the ball top of the screw.

In more detail, the polyaxial head member comprises a flattened teardrop-shaped member having a truncated acute end which includes a lower socket portion, and a through hole formed in the bulbous upper central portion. The polyaxial head member further includes a vertical split which extends upwardly from the lower socket portion, past the upper central portion which includes the through hole. The vertical split extends fully through the lower socket portion, but not fully through the upper portion so that the member is a single piece. This split divides the head member along a plane which is substantially parallel to the front and rear flat faces thereof.

In a preferred embodiment, the plane of the slot may have a slight angle as compared with the front face, extending slightly rearward as it rises. In addition, it is also preferred that the overall front-to-rear thickness of the polyaxial head member include a very slight taper such that the member is thicker at the base than at the top thereof.

The slot in the member divides the through hole into a front portion and a rear portion. The front portion includes a linear taper such that the opening is wider at the face and narrows as it approaches the vertical slot.

With respect to the socket portion, the polyaxial head member is designed to receive the ball top of the screw into the socket, the socket having substantially the same interior volume as necessary to permit the ball top to loosely rotate in the socket. As provided above, at least a portion of the socket is further split into two halves by the vertical slot. This slot renders the socket compressible (the deflection of the slot in a narrowing direction causes a decrease in the total volume of the socket, permitting the interior surface to crush lock to the ball top of the screw in the socket. The means by which the slots are deflected and the socket volume reduced is described more fully hereinbelow).

The rod gripping cross-bar member of the present invention comprises a cylindrical member having a threaded second end, a tapered middle portion, and a first end comprising a pair of opposing arcuate gripping jaw elements. More particularly, with respect to the threaded portion, the second end comprises a constant diameter cylinder that has a diameter wich is substantially similar to the constant diameter rear portion of the through hole in the polyaxial head member. The tapered middle portion has a linear tapered surface which widens from the point at which it is contiguous with the threaded end to the point at which it joins with the rod gripping first end. This linear taper has substantially the same angle of taper as the front portion of the through hole in the polyaxial head member.

The first end of the cross-bar member, which grips the rod, comprises a pair of arcuate opposing members, the inner opposing surfaces of which comprise a cylindrical receiving volume. The cross-bar member further comprises an axial split extending from the middle of the second end, through the tapered middle portion, and fully through the first end (between the opposing arcuate jaw members,) thereby rendering the inner opposing arcuate surfaces of the rod gripping end selectively deflectable into a wider or narrower position by the application of forces directed radially outward or inward on the axial slot. The total combined angle of the partial circular cross-section of the opposing jaws is greater than 180 degrees in the undeflected state, so as to permit a rod of similar diameter to be received laterally into the receiving volume only when the jaws are deflected into the widened position, and for the rod to be crush locked in the jaws by the application of an inwardly directed radial force.

The assembly and implantation of the present invention is now briefly described. The surgeon prepares the pedicle site for receiving the shaft of the screw and drives the screw into the bone. Once the screw is implanted, the cross-bar member is positioned loosely in the through holes such that the second threaded end extends through the rear portion of the through hole and the tapered middle portion is seated in the front tapered portion of the through hole. The polyaxial head is then mounted to the ball top of the screw (by permitting the vertical slot in the head to widen as the ball is inserted into the socket). At this time the head member is fully polyaxially rotatable on the ball top of the screw. Once the head has been properly positioned, the cross-bar member is axially rotated into position to receive the rod of the implant apparatus in its jaws. The rod is inserted into the cylindrical receiving volume formed by the opposing jaw members of the cross-bar element. A nut is then engaged onto the threading of the second end of the cross bar member and advanced therealong until it contacts the rear face of the polyaxial head member (the lower portion of the rear face should be contacted first in the preferred design which has a widened base of the head member). Once the nut has contacted the rear face, continued tightening causes the cross-bar member to be drawn toward the rear face, through the through hole, until the tapered middle portion of the cross bar is fully and tightly nested in the front portion of the through hole. Subsequent tightening of the nut simultaneously provides a compression of the vertical slot in the head member and the axial slot of the cross-bar member (the former compression being provided by the opposing forces between the nut against the rear face of the head member and the contact of the tapered portions of the cross-bar member and the front portion of the through hole, and the latter compression being provided by the radially inward directed forces of the front portion of the through hole against the axial split as the tapers engage). These slot compressions simultaneously lock the head to the ball top of the screw, the cross-bar member in the through hole of the polyaxial head member, and the rod in the jaws of the cross-bar member.

Multiple screw assemblies are generally necessary to complete the full array of anchoring sites for the rod immobilization system; however, the screw and coupling element assembly of the present invention is designed to be compatible with alternative rod systems so that, where necessary, the present invention may be employed to rectify the failures of other systems, the implantation of which may have already begun.

BRIEF DESCRIPTION OF THE FIGURES

FIGS. 5a and 5b are side views of a first embodiment of the polyaxial head member of the present invention mounted to the ball top of the pedicle screw illustrated in FIG. 4, wherein critical interior features of the element are shown in phantom and wherein the side views are taken along mutually perpendicular directions showing the front face and the left lateral side of the polyaxial head member respectively;

DETAILED DESCRIPTION OF THE PREFERRED EMBODIMENT

While the present invention will be described more fully hereinafter with reference to the accompanying drawings, in which particular embodiments and methods of implantation are shown, it is to be understood at the outset that persons skilled in the art may modify the invention herein described while achieving the functions and results of this invention. Accordingly, the descriptions which follow are to be understood as illustrative and exemplary of specific structures, aspects and features within the broad scope of the present invention and not as limiting of such broad scope.

Figure 2:
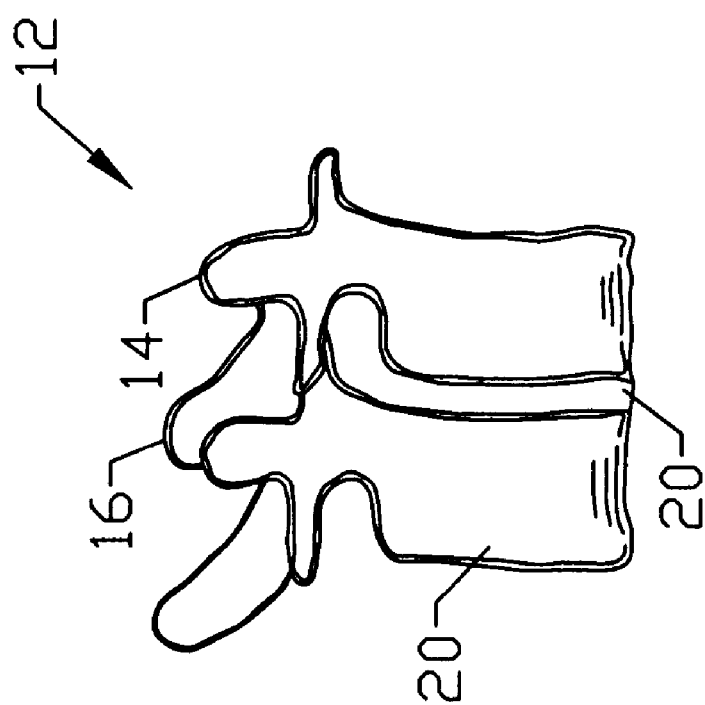
FIG. 2 is a side view of a pair of adjacent vertebrae of the type shown in FIG. 1.
Figure 1:
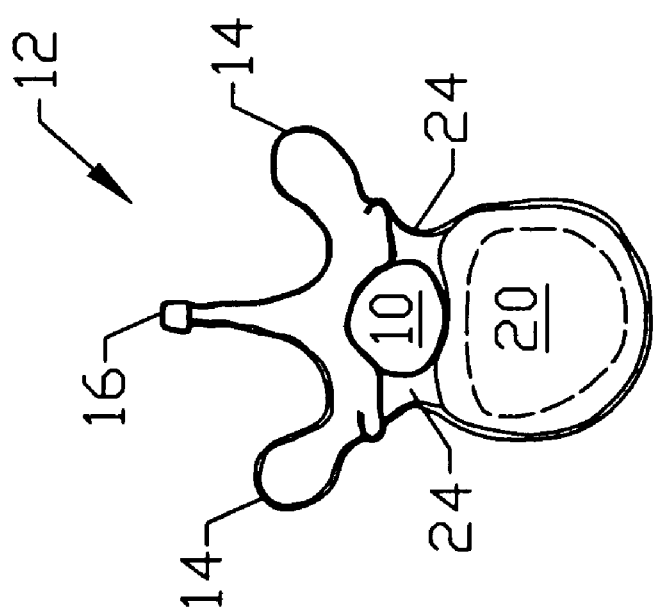
FIG. 1 is a top view of a human vertebra, which is representative of the type for which the present invention is useful for coupling thereto a rod apparatus.
Figure 3:
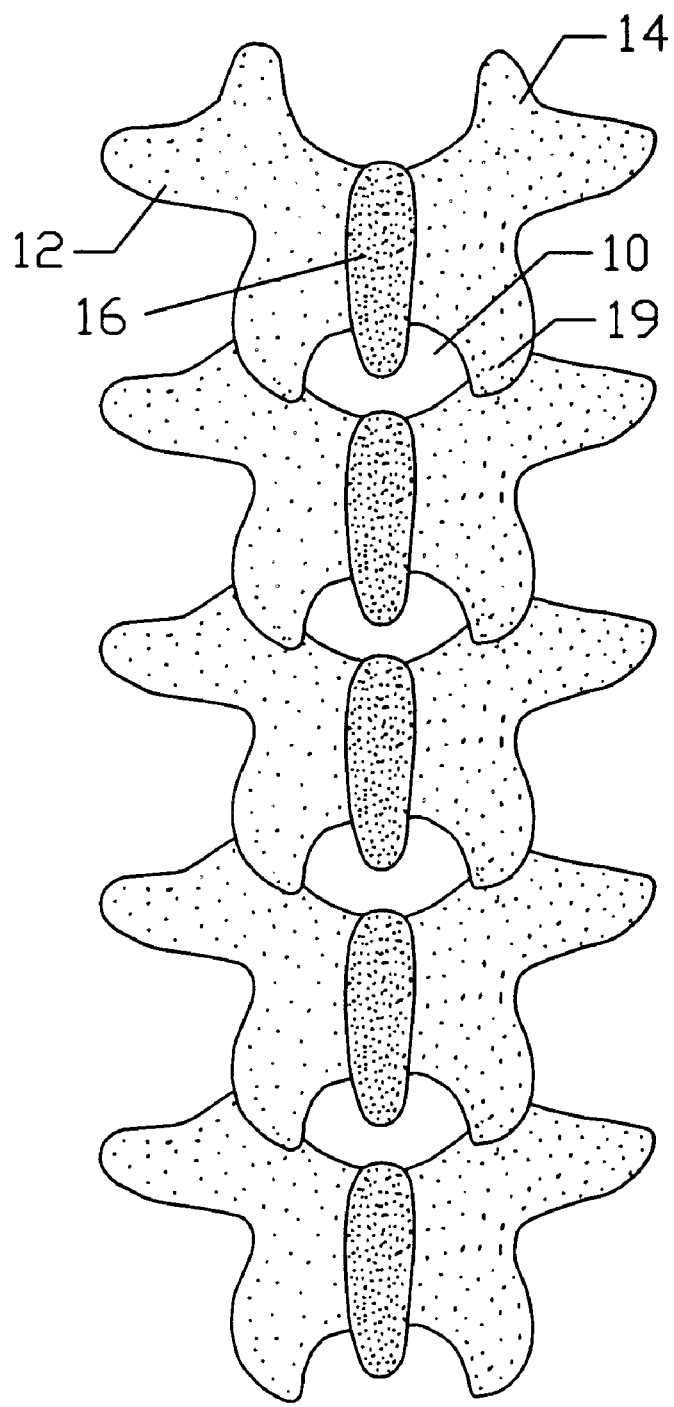
FIG. 3 is a posterior view of a sequence of vertebrae of the type shown in FIGS. 1 and 2.
Figure 4:
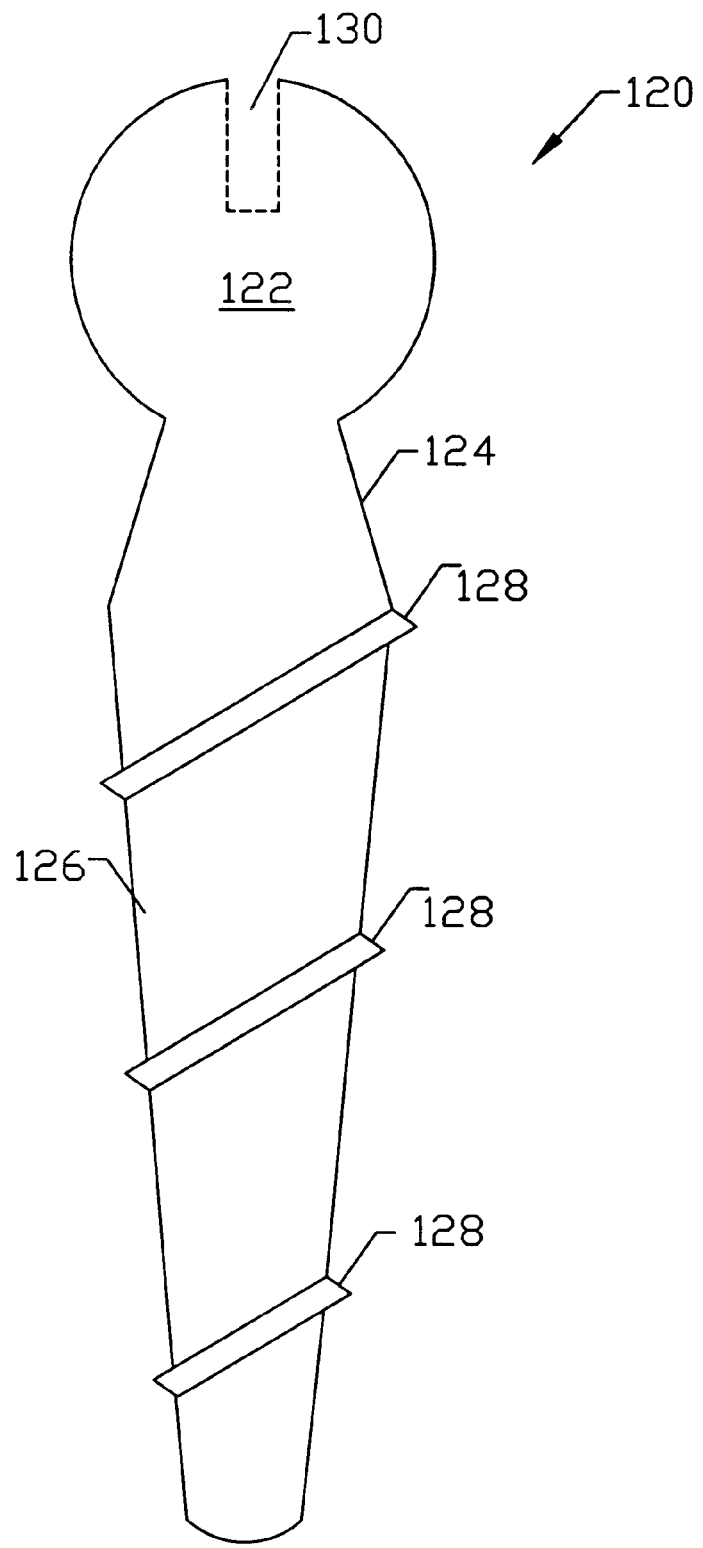
FIG. 4 is a side view of a bone screw having a ball top which is an aspect of the present invention.

Referring now to FIG. 4, a side view of the screw portion of the present invention, comprising a curvate ball top, is shown. The screw 120 comprises a ball top portion 122, a neck 124, and a shaft 126. In FIG. 4, the shaft 126 is shown as having a tapered shape with a high pitch thread 128. It shall be understood that a variety of shaft designs are interchangeable with the present design. The specific choice of shaft features, such as thread pitch, shaft diameter to thread diameter ratio, and overall shaft shape, should be made by the physician with respect to the conditions of the individual patient's bone; however, this invention is compatible with a wide variety of shaft designs.

The ball top 122 of the screw 120 comprises a semi-spherical shape, which has a recess 130 in it. It is understood that the semi-spherical shape is a section of a sphere. In the embodiment shown the section is greater in extent than a hemisphere, and it correspondingly exhibits an external contour which is equidistant from a center point of the ball top. In a preferred embodiment, the major cross-section of the semi-spherical ball top 122 (as shown in the two-dimensional illustration of FIG. 4) includes at least 270 degrees of a circle.

The recess 130 defines a receiving locus for the application of a torque for driving the screw 120 into the bone. The specific shape of the recess 122 may be chosen to cooperate with any suitable screw-driving tool. For example, the recess 130 may comprise a slot for a screwdriver, a hexagonally shaped hole for receiving an allen wrench, or most preferably, a threading for a correspondingly threaded post. It is further preferable that the recess 130 be co-axial with the general elongate axis of the screw 120, and most particularly with respect to the shaft 126. Having the axes of the recess 130 and the shaft 126 co-linear facilitates the step of inserting the screw 120 into the bone.

The semi-spherical ball top portion 122 is connected to the shaft 126 at a neck portion 124. While it is preferable that the diameter of the shaft 126 be less than the diameter of the semi-spherical ball top 122, it is also preferable that the neck 124 of the screw 120 be narrower than the widest portion of the shaft 126. This preferable dimension permits the screw to swing through a variety of angles while still being securely held in the socket of the polyaxial head member (as set forth more fully with respect to FIGS. 5a and 5b).

Referring now to FIGS. 5a and 5b, a first embodiment of the polyaxial head member 200 of the present invention is provided in front and lateral side views, respectively, in its initially polyaxial mounted position on the ball top 122 of the screw 120. More specifically with respect to the front view shown in FIG. 5a, the element 200 may be conceptually separated into a lower socket portion 202 and an upper cross-bar member receiving portion 204. The lower socket portion 202 comprises a semi-spherical interior volume 206. This interior volume 206 is accessible from the exterior through a bottom opening 208. The ball top 122 of the screw 120 is insertable into the socket 206, and is initially polyaxially rotatable within the socket through a wide range of angles which are limited only by the contact of the neck 124 of the screw against the lip 210 of the opening 208 (the diameter of the neck 124 necessarily being less than that of the opening 208).

The upper portion 204 of the polyaxial head element 200 comprises a vertical split or slot 212 which extends upwardly from the lower socket portion 202 (rendering the socket expandable and contractible), and terminates at a point 214 which is adjacent to, but below the extreme uppermost point of the head 200. At a point below the termination point 214 of the slot 212, the head further includes a through hole 216a,216b which is separated into a front portion 216a and a rear portion 216b by the vertical slot 212.

In the preferred embodiment illustrated in FIGS. 5a and 5b, the vertical slot 212 extends upward through the head 200 at a slight rearward angle. In addition, it is also preferred that the overall front-to-rear thickness of the polyaxial head member 200 include a very slight taper (the plane of the rear face forms a non-perpendicular angle with the axis of the through hole 216a,216b such that the lower portion of the rear face 217b forms an acute angle relative to the axis of the through hole). The purpose of this taper and the rearward angulation of the slot is to ensure that the slot 212 may be most effectively narrowed by the application of a compression force against the front and rear faces of the head member 200.

As suggested above, the slot 212 in the member 200 divides the through hole into a front portion 216a and a rear portion 216b. The front portion 216a is linearly tapered along the axial direction, such that the opening 218 is wider at the front face 217a and narrows as it approaches the plane of the vertical slot 212.

Figure 6A:
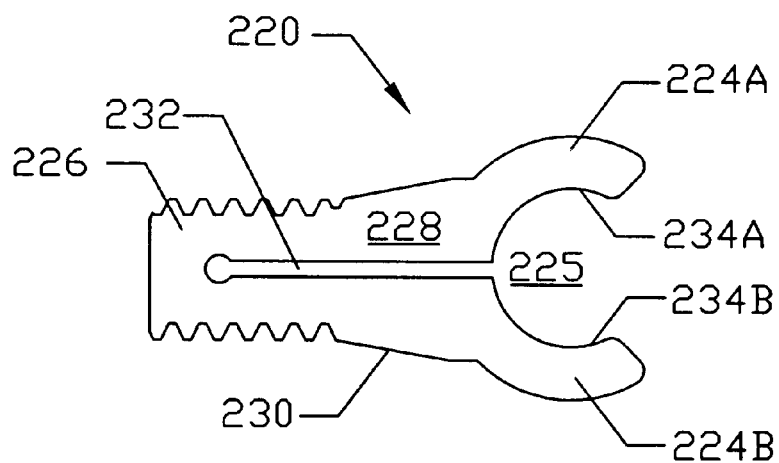
FIGS. 6a and 6b are side views of the cross-bar member of the present invention, wherein the side views are taken along mutually perpendicular directions.
Figure 6B:
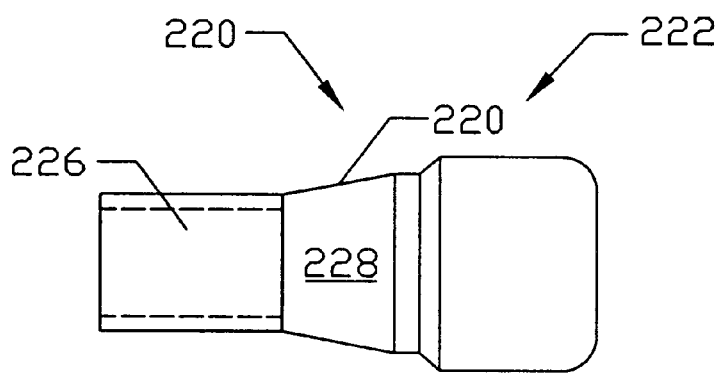

Referring now to FIGS. 6a and 6b, the rod gripping cross-bar member 220 of the present invention is provided in lateral side and top side views, respectively. The rod gripping member 220 comprises a cylindrical member having a first end 222 comprising a pair of opposing arcuate gripping jaw elements 224a,224b which together form a rod receiving channel 225; a threaded second end 226, a tapered middle portion 228. More particularly, with respect to the threaded portion 226; the second end comprises a constant diameter cylinder which has a diameter that is substantially similar to the constant-diameter rear portion 216b of the through hole in the polyaxial head member 200. The tapered middle portion 228 has a surface 230 which comprises the linear taper which widens from the point at which it is contiguous with the threaded end 226 to the point at which it joins with the rod gripping first end 222. This linear tapered surface 230 has substantially the same angle of taper as the front portion 216a of the through hole in the polyaxial head member 200.

As introduced above, first end 222 of the cross-bar member, which grips the rod, comprises a pair of arcuate opposing members 224a,224b, the inner opposing surfaces of which comprise a cylindrical receiving volume 225. The cross-bar member further comprises an axial split 232 extending from the middle of the second end 226, through the tapered middle portion 228, and fully through the first end 222 between the opposing arcuate jaw members 224a, 224b, thereby providing the means by which the inner opposing arcuate surfaces 234a,234b of the rod gripping end may deflect to widen or narrow the size of the rod receiving channel 225 by the application of forces directed radially outward or inward, respectively, on the axial slot 232. In addition, it shall be understood that the total combined angle of the partial circular cross-section of the opposing jaws 224a,224b is greater than 180 degrees in the undeflected state, thus permitting a rod of similar diameter to laterally enter the receiving volume only when the jaws 224a,224b are deflected into the widened position, and for the rod to be crush locked to the inner surfaces 234a,234b of the jaws by the application of an inwardly directed radial force.

Figure 7:
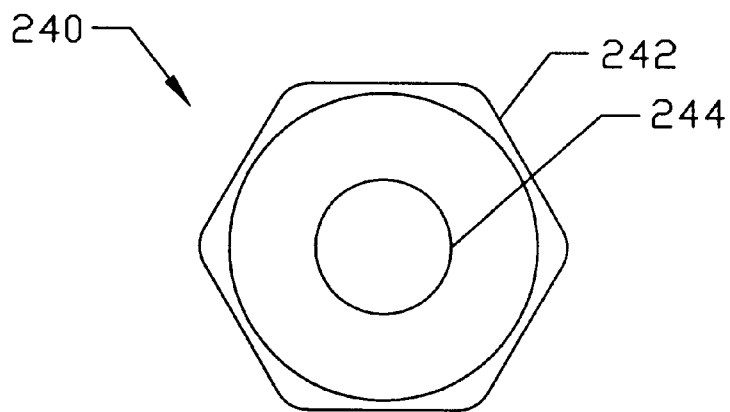
FIG. 7 is a top perspective view of the nut which is an aspect of the present invention.

Referring now to FIG. 7, the nut 240 which is provided to advance along the threaded second end 226 of the rod gripping member 220 is provided. The nut 240 is a standard nut having a hexagonal-shaped outer rim 242 and a threaded center bore 244 which is designed to receive therethrough the second end 226 of the rod gripping member 220. As set forth hereinbelow, it is the advancement of the nut 240 along this threaded second end 220 which provides the necessary forces to lock the assembly together.

Figure 8:
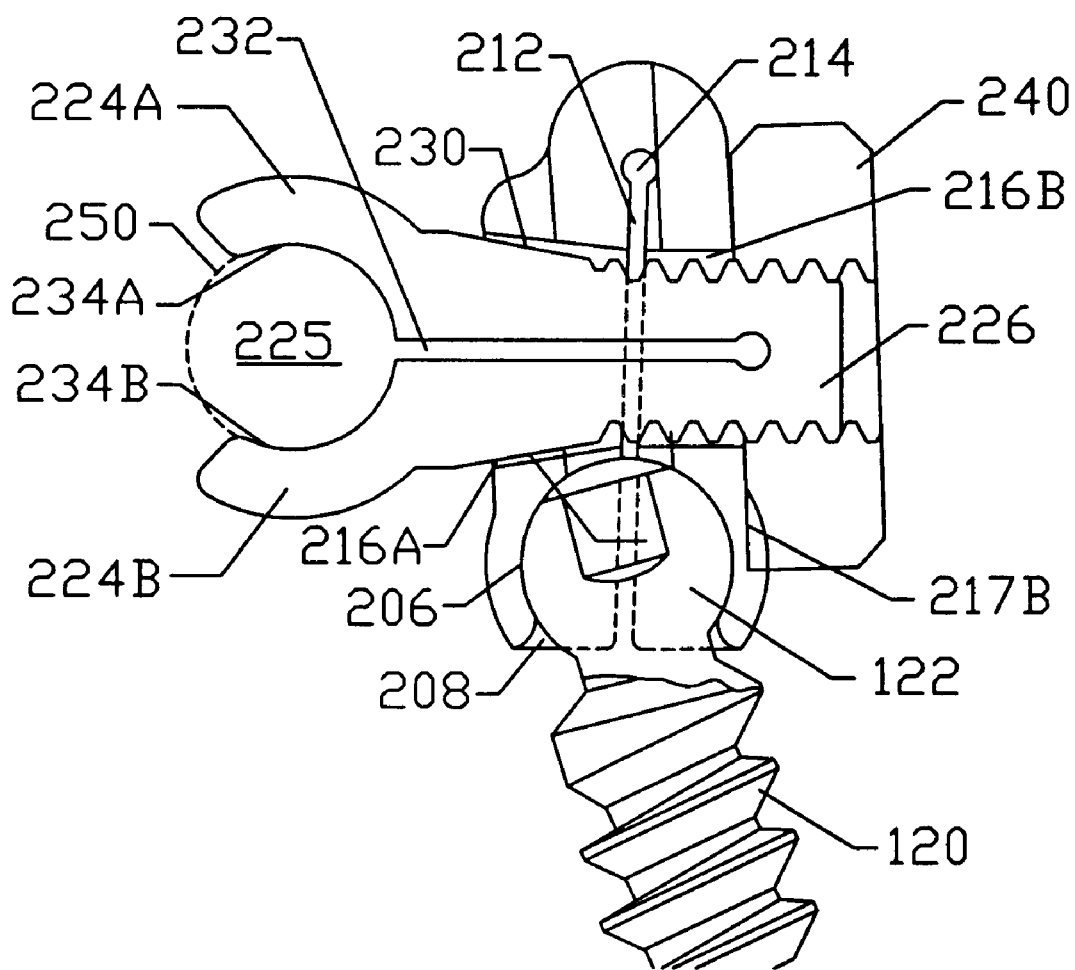
FIG. 8 is a side view of a fully assembled embodiment of the present invention.

Referring now, therefore, to FIG. 8, in which a fully locked and assembled embodiment of the present invention is provided, the assembly and implantation of the present invention is now described. The surgeon prepares the pedicle site for receiving the shaft of the screw 120 and drives the screw into the bone. Once the screw is implanted, the rod gripping cross-bar member 220 is positioned loosely in the through holes 216a,216b such that the second threaded end 226 extends through the rear portion 216b of the through hole and the tapered middle portion 228 is seated in the front tapered portion 216a of the through hole. The polyaxial head 200 is then mounted to the ball top 122 of the screw (by permitting the vertical slot 212 in the head 200 to widen as the ball 212 is inserted into the socket 202). At this time the head member is fully polyaxially rotatable on the ball top of the screw.

Once the head 200 has been properly positioned, the cross-bar member 220 is axially rotated into position to receive the rod 250 of the implant apparatus laterally between its jaws 224a,224b. The rod 250 is inserted into the cylindrical receiving volume 225 formed by the opposing jaw members of the cross-bar element 220. A nut 240 is then engaged onto the threading of the second end 226 of the cross-bar member and advanced therealong until it contacts the rear face 217b of the polyaxial head member 220 (the lower portion of the rear face should be contacted first in the preferred design which has a widened base of the head member). Once the nut 240 has contacted the rear face 217b, continued tightening causes the cross-bar member 200, and more particularly the tapered middle section 228, to be drawn deeper into the through hole, until the tapers of each (the middle portion 228 and the front portion 216a of the through hole), tightly nest. Continued tightening of the nut 240 simultaneously provides a compression of the vertical slot 212 in the head member 200 and the axial slot 232 of the cross-bar member 200. The compression of the vertical slot 212 is acheived by the opposing forces developed between the nut 240 pressing against the rear face 217b of the head member 200 and the resultant pressure of the middle tapered portion 228 of the cross-bar member 200 against the front portion 216a of the through hole. The compression of the axial slot 232 is provided by radially inward directed forces developed by the mutual engagement of the tapers of the middle tapered section 228 of the rod gripping cross-bar member 220 and the front portion 216a of the through hole. These slot compressions simultaneously lock the head 200 to the ball top 122 of the screw 120, the rod gripping cross-bar member 220 in the through hole 216a,216b of the polyaxial head member 200, and the rod 250 in the jaws 224a,224b of the cross-bar member 220.

While there has been described and illustrated an embodiment of a polyaxial screw and coupling element assembly for use with posterior spinal rod implantation apparatus, it will be apparent to those skilled in the art that variations and modifications are possible without deviating from the broad spirit and principle of the present invention. The present invention shall, therefore, be limited solely by the scope of the claims appended hereto.

We claim:

1. A spinal implant coupling assembly comprising:

a bone securing member comprising a shaft and a head;

a polyaxial head member providing a void configured to hold the head of the bone securing member during use and the polyaxial head member further comprising a through hole for engagement of a cross-bar member; and a cross-bar member, comprising deflectable arms configured to provide a channel between the arms effective to grip a spinal rod during use and wherein the cross-bar member further comprises a projection configured to pass through the through hole in the polyaxial head member;

wherein movement of the cross-bar member through the through hole provides a narrowing force on the deflectable arms and a force effective to reduce the volume of the void.

2. The assembly of claim 1, wherein the shaft of the bone securing member comprises threading.

3. The assembly of claim 1, wherein the head member provides an opening into the void configured such that, when the head of the bone securing member is disposed in the void during use, the shaft of the bone securing member passes through the opening so that the shaft is capable of polyaxially rotating with respect to the head member.

4. The assembly of claim 1, wherein the head of the bone securing member comprises a semi-spherical shape and the head member provides a spherical shaped void of substantially the same volume as the semi-spherical shaped head.

5. The assembly of claim 1, wherein the head of the bone securing member comprises a receiving locus for a driving tool.

6. The assembly of claim 5, wherein the receiving locus is a recess.

7. The assembly of claim 1, wherein the shaft is tapered to a smaller diameter toward the end distal to the head.

8. The assembly of claim 1, wherein the head member comprises a lower portion, an upper portion, and a compressible slot extending entirely through the lower portion and terminating in the upper portion, configured so that compression of the slot decreases the volume of the void.

9. The assembly of claim 1, wherein the through hole is tapered such that advancement of the cross-bar member through the through hole provides a force effective to deflect the arms together and decrease the size of the channel between the arms.

10. The assembly of claim 1, wherein the cross-bar member comprises a connecting region disposed between the arms and the projection and wherein the connecting region is tapered such that advancement of the cross-bar member through the through hole provides a force effective to deflect the arms together and decrease the size of the channel between the arms.

11. The assembly of claim 1, wherein the projection comprises threading and wherein the cross-bar member is advanceable through the through hole by turning a nut on the threading during use.

12. The assembly of claim 1, wherein the cross-bar member comprises a compressible slot extending from the channel formed between the arms into the projection.

13. The assembly of claim 1, wherein the bone securing member comprises a neck region between the shaft and the head, and wherein the neck region has a smaller diameter than the shaft adjacent the neck region.

14. The assembly of claim 1, further comprising a spinal rod.

15. An orthopedic implant apparatus, comprising:
a posterior spinal implant assembly;
a pedicle bone screw comprising a head and a shaft;
a cross-bar member comprising deflectable arms configured to grip a spinal implant assembly, a projection and a connecting region disposed between the arms and the projection; and
a connector for connecting the bone screw to the cross-bar member, the connector having a first opening and a second formed therein;
wherein the head of the bone screw is configured to fit in a polyaxially rotatable engagement within the connector in the first opening, and wherein the projection of the cross-bar member is configured to pass through the second opening within the connector, and further wherein advancement of the projection through the second opening in the cross-bar member is effective to compression lock the arms to the spinal implant assembly and to compression lock the head of the bone screw in the first opening during use.

16. The apparatus of claim 15, wherein the projection comprises threading and wherein the apparatus comprises a nut, threadable on the projection.

17. A method for implanting an orthopedic coupling assembly, comprising:
providing an apparatus comprising:
a posterior spinal implant assembly;
a pedicle bone screw comprising a head and a shaft;
a cross-bar member comprising deflectable arms configured to grip a spinal implant assembly, a projection and a connecting region disposed between the arms and the projection; and
a connector for connecting the bone screw to the cross-bar member, the connector having a first and a second opening formed therein;
implanting the pedicle bone screw into a bone;
inserting the projection of the cross-bar member into the first opening in the connector;
inserting a head of the pedicle bone screw into the second opening in the connector;
positioning a portion of a posterior spinal implant assembly in the cross-bar member; and
advancing the cross-bar member into the first opening effective to compression lock the cross-bar member to the posterior spinal implant assembly and to compression lock the head of the pedicle bone screw in the second opening of the connector.

18. The method of claim 17, wherein the first opening comprises a from tapered portion and a rear portion; and wherein the cross-bar member comprises a first end, a tapered middle portion, and a second end; and wherein inserting the cross-bar member into the first opening comprises positioning the cross-bar member in the first opening such that the second end extends through the rear portion of the first opening and such that the tapered middle portion is seated in the front tapered portion of the first opening.

19. The method of claim 17, wherein the cross-bar member comprises opposed jaw members, and wherein positioning a portion of the posterior spinal implant assembly in the cross-bar member comprises:
axially rotating the cross-bar member such that the cross-bar member is positioned to receive a portion of the posterior spinal implant assembly in a receiving volume formed by the opposed jaw members; and
inserting the portion of the posterior spinal implant assembly into the receiving volume.

20. The method of claim 17, wherein the cross-bar member comprises a first end, a tapered middle portion, and a threaded second end; and wherein advancing the cross-bar member into the first opening comprises:
engaging a nut onto the threaded second end of the cross-bar member;
advancing the nut along the second end until the nut contacts a rear face of the connector; and
tightening the nut against the connector.

* * * * *

UNITED STATES PATENT AND TRADEMARK OFFICE
CERTIFICATE OF CORRECTION

PATENT NO. : 5,997,539
DATED : December 7, 1999
INVENTOR(S) : Joseph P. Errico, Thomas J. Errico, James D. Ralph, Stephan Tatar It is certified that error appears in the above-identified patent and that said Letters Patent is hereby corrected as shown below:

In the Claims:

Claim 15, col. 9, line 36, after the word "second" add the word --opening--.
Claim 17, col. 10, line 8, after the word "first" add the word --opening--.

Signed and Sealed this

Twelfth Day of December, 2000

Attest:

Attesting Officer

Q. TODD DICKINSON
Director of Patents and Trademarks